United States Patent [19]

Okayama

[11] Patent Number: 4,583,070
[45] Date of Patent: * Apr. 15, 1986

[54] SILANE GAS SENSOR AND A METHOD OF MAKING THE SAME

[75] Inventor: Yoshiaki Okayama, Yamato, Japan

[73] Assignee: Nohmi Bosai Kogyo Co., Ltd., Tokyo, Japan

[*] Notice: The portion of the term of this patent subsequent to Sep. 24, 2002 has been disclaimed.

[21] Appl. No.: 595,380

[22] Filed: Mar. 30, 1984

[30] Foreign Application Priority Data

Aug. 31, 1983 [JP] Japan .................. 58-157931

[51] Int. Cl.[4] .................. H01L 7/00; G01N 27/04
[52] U.S. Cl. .......................... 338/34; 73/23; 427/126.3
[58] Field of Search ............ 427/126.3; 338/34, 35; 73/23, 29

[56] References Cited

U.S. PATENT DOCUMENTS

| 4,000,089 | 12/1976 | Senda ................ 338/34 X |
| 4,001,758 | 1/1977 | Esper et al. ............ 338/34 |
| 4,033,169 | 7/1977 | Fujishiro et al. ....... 338/34 X |
| 4,224,280 | 9/1980 | Takahama et al. ...... 338/34 X |
| 4,242,303 | 12/1980 | Takahashi et al. ..... 338/34 X |
| 4,251,225 | 2/1981 | Handa et al. ........... 338/34 X |
| 4,359,709 | 11/1982 | Nakatani et al. ....... 338/34 |
| 4,417,228 | 11/1983 | Takami et al. .......... 338/34 |

*Primary Examiner*—John F. Niebling
*Assistant Examiner*—Nam X. Nguyen
*Attorney, Agent, or Firm*—Wenderoth, Lind & Ponack

[57] ABSTRACT

A sensor for detecting low concentrations of silane gas in air and a process for making the sensor are disclosed. The sensor comprises a silane-sensitive element and a heater to heat the element to 200°–400° C. The element comprises an electrode-equipped alumina porcelain tube coated with a mixture of $SnO_2$, SbOCl, and Pt. The tube is calcined in air or in an oxidized antimony atmosphere at 600°–850° C. and is exposed to a silane atmosphere at 150°–850° C. to stabilize its properties.

5 Claims, 3 Drawing Figures

SILANE GAS SENSOR AND A METHOD OF MAKING THE SAME

BACKGROUND OF THE INVENTION

This invention relates to a sensor for detecting low concentrations of silane gas in the air and to a method of manufacturing the same.

In semiconductor factories, chemical factories, laboratories, and the like, large quantities are used of certain gases which can spontaneously ignite and combust upon contacting or mixing with air or other gases even when existing in concentrations of a few percent. Examples of these gases are monosilane ($SiH_4$), dichlorosilane ($SiH_2Cl_2$), trichlorosilane ($SiHCl_3$), phosphine ($PH_3$), diborane ($B_2H_6$), and arsenic hydride ($AsH_3$). There are increasing incidents of fires caused by the leaking of such gases into the atmosphere followed by their spontaneous ignition. For this reason, there is a great need for a gas sensor which can detect low concentrations of these gases. However, up to the present time, no such sensor has been developed.

In Japanese Patent Application No. 57-226510, the present inventors disclosed as element for sensing carbon monoxide prepared by mixing stannic oxide ($SnO_2$), antimony oxychloride (SbOCl), and chloroplatinic acid ($H_2PtCl_6$) so that the molar ratio of Sb to Sn is 0.02–0.08 and the molar ratio of Pt to Sn is 0.02–0.10 and calcining the mixture in air or in an oxidized antimony atmosphere at 600°–850° C.

In the course of experiments, the present inventors discovered that if a heating means were added to the carbon monoxide sensor described above and the sensor were thereby heated to 260° C., the resulting apparatus had a high selectivity for monosilane gas ($SiH_4$).

Specifically, in their experiments, the present inventors prepared a mixture of $SnO_2$, $H_2PtCl_6$, and SbOCl with a Pt/Sn molar ratio of 0.04 and an Sb/Sn molar ratio of 0.06 and coated this mixture on two alumina porcelain tubes each having a pair of electrodes. The tubes were then calcined at 700±5° C. for 15 minutes either in air or in a quartz tube containing an oxidized antimony gas prepared by calcining 4.0 mg of SbOCl. Electrical heating means were then inserted into the alumina porcelain tubes and a voltage was applied to the heaters to heat the tubes to 260° C. The electrical resistance between the electrodes of each tube was then measured in clean air at 25° C. and then again in each of eight different samples of air at 25° C. each containing 100 ppm of either CO, $CH_4$, $C_2H_4$, $C_2H_6$, $H_2$, $NH_3$, EtOH, or $SiH_4$. Measurement in $SiH_4$ was carried out last. The results of these measurements are shown in Table 1 in the form $R_o/R_g$, where $R_o$ is the initial electrical resistance in air and $R_g$ is the electrical resistance in a particular gas mixture. In the table, Sensor A is the sensor formed using the tube which was calcined in air and Sensor B is the sensor formed using the tube which was calcined in the aforementioned oxidized antimony gas.

TABLE 1

| ATMOSPHERE | | SENSOR A $R_o/R_g$ | SENSOR B $R_o/R_g$ |
| --- | --- | --- | --- |
| CO | 100 ppm | 1.2 | 1.3 |
| $CH_4$ | 100 ppm | 1.1 | 1.2 |
| $C_2H_4$ | 100 ppm | 1.3 | 1.1 |
| $C_2H_6$ | 100 ppm | 1.2 | 1.1 |
| $H_2$ | 100 ppm | 1.2 | 1.5 |

TABLE 1-continued

| ATMOSPHERE | | SENSOR A $R_o/R_g$ | SENSOR B $R_o/R_g$ |
| --- | --- | --- | --- |
| $NH_3$ | 100 ppm | 8 | 7 |
| EtOH | 100 ppm | 24 | 25 |
| $SiH_4$ | 100 ppm | 145 | 130 |

The initial resistance in air $R_o$ was 135 kilohms for Sensor A and 74 kilohms for Sensor B. It was found that exposure to the first seven gases in the table did not significantly effect the resistance in air, but that after exposure to $SiH_4$ gas, the resistance in air ($R_{air}$) upon the second measurement fell to 28 kilohms for Sensor A and to 16.5 kilohms for Sensor B.

After the second measurement of resistance in clean air, the resistance in each gas was again measured. This time, for Sensor A, $R_{air}/R_g$ was 36 in $SiH_4$, 5.8 in EtOH, and 1.1–3.6 in the other gases, while for Sensor B, $R_{air}/R_g$ was 33 in $SiH_4$, 6.3 in EtOH, and 1.1–3.8 in the other gases.

For the third and subsequent measurements of resistance, for both Sensor A and Sensor B the resistance in air $R_{air}$ showed almost no change between measurements, $R_{air}/R_g$ in $SiH_4$ was 18–27, and the values of $R_{air}/R_g$ in the other gases were substantially the same as or lower than those given above.

The above experiment was repeated using different calcining temperatures and different compositions for the mixture coated on the tubes. The value of $R_{air}/R_g$ in $SiH_4$ was 110–300 for the first measurement, 30–50 for the second measurement, and 16–35 for subsequent measurements, while the values of $R_{air}/R_g$ in other gases were ¼–1/6 of the values in $SiH_4$.

The silane gas sensor achieved by adding a heater to the carbon monoxide sensing element of Japanese Application No. 57-226510 and heating the apparatus at 200°–400° C. thus has a high selectivity for gaseous silanes. Although the change over time of the value of $R_{air}/R_g$ for gaseous silanes is initially large, if the sensor is once exposed to gaseous silanes, the change over time of $R_{air}/R_g$ becomes small and tends to reach a stable value.

SUMMARY OF THE INVENTION

It is the object of the present invention to provide a sensor for detecting silane gases which can detect even low concentrations of gaseous silanes in the air.

It is another object of the present invention to provide a sensor for silane gases which exhibits only a small change in its sensitivity over use.

A silane gases sensor according to the present invention is basically the carbon monoxide sensor of Japanese Application No. 57-226510 to which a heater has been added and which has been exposed to silane gas in order to stabilize its sensitivity to silanes.

A sensor for silane gas according to the present invention comprises a silane-sensitive element prepared by mixing $SnO_2$, SbOCl, and Pt such that the molar ratio of Sb to Sn is approximately 0.02–0.08 and the molar ratio of Pt to Sn is approximately 0.02–0.10, and calcining the mixture at 600°–850° C. in either air or an oxidized antimony gas atmosphere, and further comprises a heating means for heating the element to 200°–400° C.

A method for making a silane gas sensor according to the present invention comprises the following steps:

(a) adding an aqueous solution of $H_2PtCl_6$ to $SnO_2$ so that the molar ratio of Pt/Sn is approximately 0.02-0.10, thoroughly dispersing the $SnO_2$ in the $H_2PtCl_6$, followed by freezing and vacuum drying of the resulting dispersion;

(b) mixing SbOCl with the product of Step (a) so that the molar ratio of Sb to Sn in the resulting mixture is approximately 0.02-0.08;

(c) adding an organic solvent to the product of Step (b), forming the resulting mixture into a paste, coating the paste on an electrical insulator having electrodes, and drying the coated paste;

(d) calcining the coated insulator produced in Step (c) at approximately 600°-850° C. in an oxidized antimony atmosphere; and (e) exposing the calcined insulator of Step (d) to a silane atmosphere.

DESCRIPTION OF THE PREFERRED EMBODIMENTS

Figure 1:
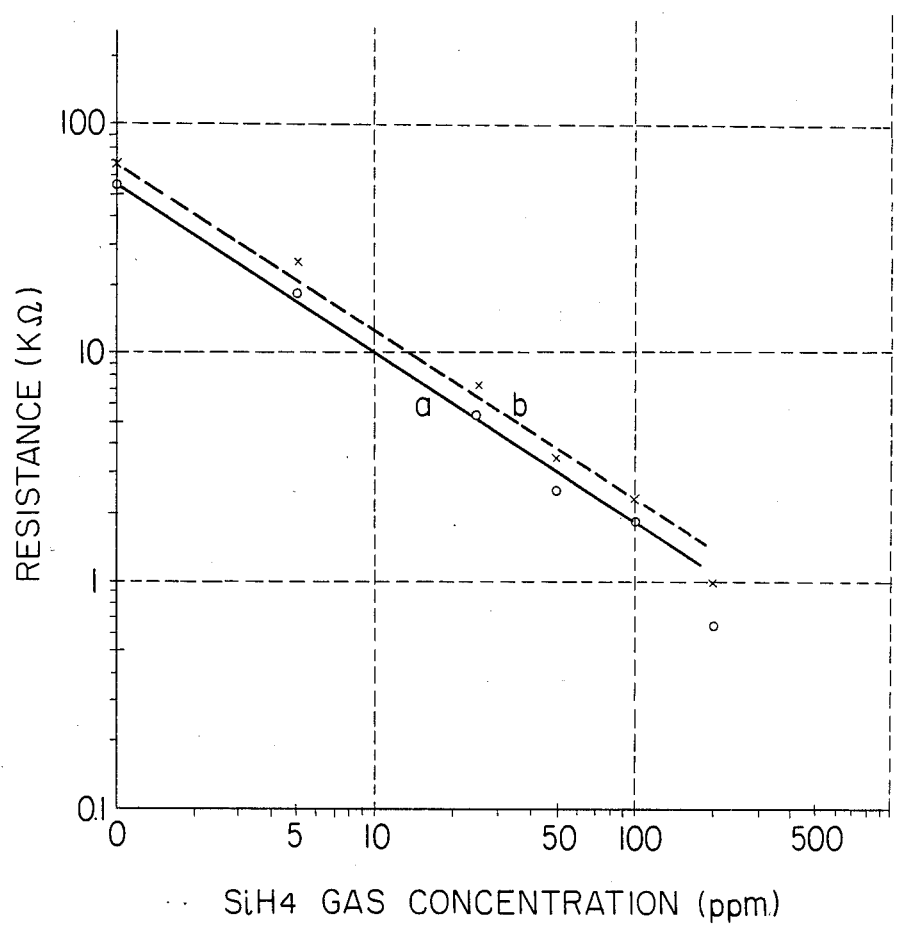
FIG. 1 is a graph of the electrical resistance in various concentrations of $SiH_4$ gas of two different gas sensors according to the present invention.
Figure 2:
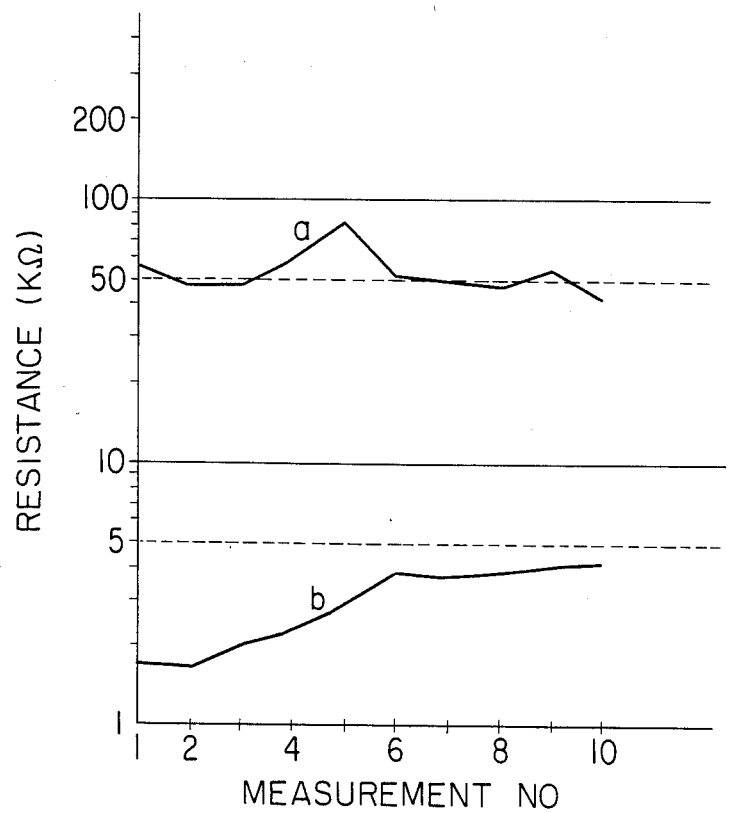
FIG. 2 is a graph of the change in electrical resistance as a function of the number of times used of a silane gas sensor according to the present invention which was calcined in air. Curve (a) shows the resistance in clean air and Curve (b) shows the resistance in $SiH_4$ gas.
Figure 3:
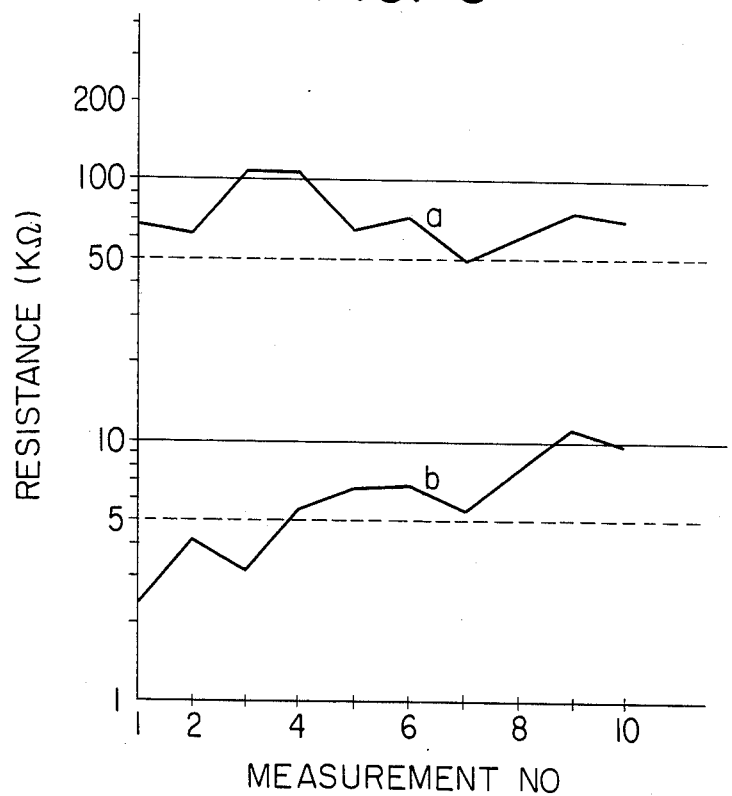
FIG. 3 is a graph of the change in electrical resistance as a function of the number of times used of a silane gas sensor according to the present invention which was calcined in an oxidized antimony gas atmosphere. Curve (a) shows the resistance in clean air and Curve (b) shows the resistance in $SiH_4$ gas.

A silane gas sensor according to the present invention and a method for manufacturing this sensor will now be explained in connection with the following illustrated examples.

EXAMPLE 1

An aqueous solution of $H_2PtCl_6$ was added to $SnO_2$ in an amount such that the molar ratio of Pt to Sn was 0.04 and the $SnO_2$ was well dispersed using ultrasonic waves. The aqueous dispersion was quick frozen at $-40°$ C. and then dried in a vacuum freeze dryer. SbOCl was then added to the dried product in an amount such that the molar ratio of Sb to Sn was 0.04, and the two were mixed with a mortar for 30 minutes. Isopropyl alcohol was then added to the mixture to form a paste, and the paste was then coated on an alumina porcelain tube equipped with electrodes and dried by natural drying. After the paste had dried, the tube was placed into a quartz tube containing air preheated to $700°-\pm5°$ C. and calcined for 30 minutes. After calcining, an electric heater was installed inside the porcelain tube, and a current was passed through the heater so as to heat the tube to $300°$ C.$\pm50°$ C. In this heated condition, the tube was aged in air for 12 hours. After aging, the tube was heated to $325\pm5°$ C. using the heater and was exposed to a silane gas atmosphere containing 100 ppm $SiH_4$ for 10 minutes in order to stabilize the characteristics of the sensor. Finally, the complete gas sensor, the tube was heated to $300\pm50°$ C. by the heater and the tube was aged for 12 hours in air.

Sixteen identical gas sensors were prepared according to the above method. The sensors were then heated to $325°$ C. by the heaters and were exposed to clean air at $25°$ C. and to each of 8 different gas mixtures containing either 100 ppm of $SiH_4$, EtOH, or CO, or 1000 ppm, of $H_2$, $CH_4$, $C_2H_4$, $C_2H_6$, $NH_3$. Exposure to air was carried out first, and exposure to the $SiH_4$ gas atmosphere was carried out last. The electrical resistance between the electrodes of each of the sensors was measured in each of the atmospheres. The results of the measurements are shown in Table 2 in the form $R_o/R_g$, where as before $R_o$ is the initial resistance in air and $R_g$ is the resistance in the gas. The values in the table are the averages for 16 sensors.

TABLE 2

| ATMOSPHERE | | $R_o/R_g$ |
|---|---|---|
| CO | 100 ppm | 2.5 |
| $CH_4$ | 1000 ppm | 1.3 |
| $C_2H_4$ | 1000 ppm | 2.3 |
| $C_2H_6$ | 1000 ppm | 1.5 |
| $H_2$ | 1000 ppm | 2.0 |
| $NH_3$ | 1000 ppm | 2.4 |
| EtOH | 100 ppm | 5.2 |
| $SiH_4$ | 100 ppm | 31 |

The maximum value of $R_o$ was 91 kilohms and the minimum was 35 kilohms. The maximum value of $R_9$ in the $SiH_4$ gas atmosphere was 3.3 kilohms and the minimum value was 0.9 kilohms.

Next, the 16 sensors were exposed to different concentrations of $SiH_4$ gas. The values of $R_g$ in the different concentrations are plotted as Curve (a) of FIG. 1.

EXAMPLES 2-24

Using the same method as for Example 1, sensors having various values of the Pt/Sn molar ratio, the Sb/Sn molar ratio, the calcining temperature in air, the temperature for exposure to the $SiH_4$ gas atmosphere, and the concentration of the $SiH_4$ during exposure were prepared. The characteristics and preparation conditions of the examples are shown in Table 3. Examples 17-24 were comparative examples. For the comparative examples, either the composition or the preparation conditions were outside the limits prescribed for the present invention. The asterick marks in Table 3 indicate which item was not in accordance with the present invention. Example 1 of Table 2 and Example 1 of Table 3 represent different batches of sensors prepared using the same method.

TABLE 3

| Example No. | Pt/Sn X-100 | Sb/Sn X-100 | Calcining Temp. (°C.) | Sensor in Silane (°C.) | Silane Conc. (ppm) | R0/Rg1 (25° C.) | Rg10/Rg1 (25° C.) | R0/Rg10 (25°C.) |
|---|---|---|---|---|---|---|---|---|
| 1 | 4 | 4 | 700 | 325 | 100 | 30 | 3.3 | 9.1 |
| 2 | 4 | 6 | 600 | 325 | 100 | 37 | 3.8 | 9.7 |
| 3 | 4 | 6 | 700 | 325 | 100 | 31 | 3.0 | 10.3 |
| 4 | 4 | 6 | 850 | 325 | 100 | 16 | 3.3 | 4.9 |
| 5 | 4 | 2 | 700 | 325 | 100 | 22 | 4.0 | 5.5 |
| 6 | 4 | 8 | 700 | 325 | 100 | 27 | 3.2 | 8.4 |
| 7 | 2 | 6 | 700 | 325 | 100 | 18 | 3.5 | 5.1 |

TABLE 3-continued

| Example No. | Pt/Sn X-100 | Sb/Sn X-100 | Calcining Temp. (°C.) | Sensor in Silane (°C.) | Silane Conc. (ppm) | $R_0/R_{g1}$ (25° C.) | $R_{g10}/R_{g1}$ (25° C.) | $R_0/R_{g10}$ (25°C.) |
| --- | --- | --- | --- | --- | --- | --- | --- | --- |
| 8  | 8   | 6   | 700  | 325 | 100   | 23 | 3.3 | 7.0 |
| 9  | 10  | 6   | 700  | 325 | 100   | 23 | 4.0 | 5.8 |
| 10 | 4   | 6   | 700  | 150 | 100   | 25 | 3.3 | 7.6 |
| 11 | 4   | 6   | 700  | 200 | 100   | 27 | 3.1 | 8.7 |
| 12 | 4   | 6   | 700  | 500 | 100   | 21 | 3.2 | 6.6 |
| 13 | 4   | 6   | 700  | 850 | 100   | 15 | 3.5 | 4.3 |
| 14 | 4   | 6   | 700  | 325 | 25    | 35 | 5.0 | 7.0 |
| 15 | 4   | 6   | 700  | 325 | 500   | 24 | 3.2 | 7.5 |
| 16 | 4   | 6   | 700  | 325 | 1000  | 12 | 3.3 | 3.6 |
| 17 | 4   | 6   | 550* | 325 | 100   | 41 | 8.5 | 4.8 |
| 18 | 4   | 6   | 900* | 325 | 100   | 9  | 4.1 | 2.2 |
| 19 | 4   | 1*  | 700  | 325 | 100   | 12 | 7.0 | 1.7 |
| 20 | 4   | 10* | 700  | 325 | 100   | 9  | 3.6 | 2.5 |
| 21 | 1*  | 6   | 700  | 325 | 100   | 8  | 5.5 | 1.5 |
| 22 | 12* | 6   | 700  | 325 | 100   | 22 | 6.0 | 3.7 |
| 23 | 4   | 6   | 700  | 325 | 10*   | 50 | 12  | 4.2 |
| 24 | 4   | 6   | 700  | 325 | 1500* | 5  | 2.5 | 2.0 |

For each example, 16 sensors were prepared. As was done in Example 1, each of the sensors was preheated to 325° C. by its heater and then exposed to clean air at 25° C. and then to 100 ppm of SiH₄ gas at 25° C., and the electrical resistance between the electrodes of each sensor was measured in both atmospheres. The process of measurement in air followed by measurement in SiH₄ gas was carried out ten times for each sensor.

The results of measurement are shown in Table 3 in the form $R_o/R_{g1}$, $R_{g10}/R_{g1}$, and $R_o/R_{g10}$, where $R_o$ is the electrical resistance upon the first measurement in air, $R_{g1}$ is the electrical resistance upon the first measurement in SiH₄ gas, and $R_{g10}$ is the electrical resistance in SiH₄ upon the 10th measurement. $R_o/R_{g1}$ is an indication of the initial sensitivity of the sensor to SiH₄ gas. A value of 10.0 or above is desirable. $R_{g10}/R_{g1}$ is an indication of the stability of the sensor and is desirably 5.5 or less. $R_o/R_{g10}$ is an indication of the sensitivity of a sensor to SiH₄ after being used numerous times, and is desirably 3.0 or above.

The values shown in Table 3 are the averages of 16 sensors. It can be seen that all of the examples of gas sensors according to the present invention (Examples 1-16) shown in Table 3 had good sensitivity to SiH₄ gas, both initially and after 10 measurements, and thus showed good stability.

However, as can been seen from the results for the comparative examples, if the Pt to Sn molar ratio is greater than approximately 0.10 (Example 22), the resulting sensors have a large change in sensitivity to SiH₄ gas, as indicated by a large value for $R_{g10}/R_{g1}$. On the other hand, if the Pt to Sn molar ratio is less than approximately 0.02 (Example 21), the initial sensitivity to SiH₄ gas, expressed by $R_o/R_{g1}$, is too low.

If the molar ratio of Sb to Sn is less than approximately 0.02 (Example 19), the value of $R_{g10}/R_{g1}$ is too large, whereas if the molar ratio is greater than approximately 0.08 (Example 20), the value of $R_o/R_{g1}$ is too small.

If the calcining temperature in air of a sensor is below approximately 600° C. (Example 17), the value of $R_{g10}/R_{g1}$ is too high, whereas if the calcining temperature is above approximately 850° C. (Example 18), the value of $R_o/R_{g1}$ is too low.

The concentration of silane gas to which a sensor prepared according to the present invention is exposed is defined as being approximately 25 ppm–1000 ppm. If the concentration falls below this range (Example 23), the value of $R_{g10}/R_{g1}$ is too high, whereas if too high a concentration is used (Example 24), the value of $R_o/R_{g1}$ is too low.

All of the preceding examples involved calcining in air. However, a silane gas sensor according to the present invention can also be prepared by calcining in an oxidized antimony atmosphere. The following examples illustrate silane gas sensors according to the present invention prepared by this second method.

EXAMPLE 25

In a manner similar to that used for Example 1, an aqueous solution of H₂PtCl₆ was added to SnO₂ in an amount such that the molar ratio of Pt to Sn was 0.04 and the SnO₂ was well dispersion using ultrasonic waves. The dispersed was quick frozen at −40° C. and then dried in a vacuum freeze layer. SbOCl was then added to the dried product in an amount such that the molar ratio of Sb to Sn was 0.04, and the two were mixed with a mortar for 30 minutes. Isopropyl alcohol was then added to the mixture to form a paste, and the paste was then coated on an alumina porcelain tube equipped with electrodes and dried by natural drying.

Up until this point, the method was identical to that used in Example 1. However, instead of performing calcining in air as in Example 1, calcining was instead performed in an oxidized antimony atmosphere. The oxidized antimony atmosphere was prepared by preheating a quartz tube (I.D.=40 mm, length of the portion of tube lying within an electric furnace=500 mm) to 700±5° C. in an electric furnace. An alumina boat holding 2.5 mg of SbOCl was then encapsulated in the quartz tube and heated for 30 minutes to produce an atmosphere of oxidized antimony therein. Although the ends of the quartz tube extended outside of the electric furnace, the oxidized antimony atmosphere was substantially confined to the 500 mm inside the furnace, so that the effective volume of the quartz tube was 628 cm³. The concentration of oxidized antimony in the quartz tube was $2.3\times10^{-8}$ moles/cm³.

The naturally dried alumina porcelain tube was then encapsulated in the quartz tube and calcined in the oxidized antimony atmosphere at 700±5° C. for 30 minutes.

After calcining, the alumina porcelain tube was removed from the quartz tube and an electric heater was installed therein. Then, as in the method used for Example 1, the porcelain tube was heated to 300±50° C. by the heater and aged in air for 12 hours. After aging, the tube was heated to 325±5° C. using the heater and was exposed to a silane gas atmosphere containing 100 ppm $SiH_4$ for 10 minutes in order to stabilize the characteristics of the sensor. After exposure to $SiH_4$ gas, the porcelain tube was again heated to 300±50° C. and aged in air for 12 hours. At the end of aging, the silane gas sensor was complete.

Sixteen sensors were prepared in this manner. The sensors were then heated to 325° C. by their heaters and then exposed to clean air at 25° C. and then to eight different atmospheres at 25° C. containing 100 ppm of gaseous EtOH, CO, $H_2$, $CH_4$, $C_2H_4$, $C_2H_6$, $NH_3$, or $SiH_4$. In each atmosphere, the electrical resistance between the electrodes of each sensor was measured. The average results are shown in Table 4 in the form $R_o/R_g$, where $R_o$ is the initial electrical resistance in clean air and $R_g$ is the electrical resistance in a particular atmosphere. Measurement was carried out first in air and last in the $SiH_4$ gas atmosphere.

TABLE 4

| ATMOSPHERE | | $R_o/R_g$ |
| --- | --- | --- |
| CO | 100 ppm | 4.6 |
| $CH_4$ | 100 ppm | 1.4 |
| $C_2H_4$ | 100 ppm | 2.1 |
| $C_2H_6$ | 100 ppm | 1.6 |
| $H_2$ | 100 ppm | 6.3 |
| $NH_3$ | 100 ppm | 2.1 |
| EtOH | 100 ppm | 6.0 |
| $SiH_4$ | 100 ppm | 30 |

The maximum value of $R_o$ for the 16 sensors was 110 kilohms and the minimum value was 43 kilohms. The maximum value of $R_g$ in 100 ppm of $SiH_4$ gas was 3.7 kilohms and the minimum was 1.1 kilohms. As can be seen from Table 4, the sensors had excellent sensitivity to $SiH_4$ gas.

The electrical resistance of these sensors was also measured in different concentrations of $SiH_4$ gas. The results are plotted as Curve (b) of FIG. 1.

EXAMPLES 26–48

Using basically the same method as for Example 25, examples of gas sensors were prepared using various values for the Pt to Sn molar ratio, the Sb to Sn molar ratio, the calcining temperature in the oxidized antimony atmosphere, the temperature of the silane gas atmosphere to which each sensor was exposed during preparation, and the concentration of $SiH_4$ in the silane gas atmosphere. The composition and preparation conditions for each of the examples are shown in Table 5. Examples 41–48 were comparative examples in which either the composition or preparation conditions fell outside of the bounds prescribed for the present invention. Those items falling outside the prescribed bounds are marked by asterick marks in the table. Example 25 of Table 4 and Example 25 of Table 5 represent different batches of the same sensor.

TABLE 5

| Example No. | Pt/Sn X-100 | Sb/Sn X-100 | Calcining Temp. (°C.) (antimony) | Sensor in Silane (°C.) | Silane Conc. (ppm) | R0/Rg1 (25° C.) | Rg10Rg1 (25° C.) | R0/Rg10 (25° C.) |
| --- | --- | --- | --- | --- | --- | --- | --- | --- |
| 25 | 4 | 4 | 700 | 325 | 100 | 33 | 3.9 | 8.5 |
| 26 | 4 | 6 | 600 | 325 | 100 | 35 | 4.5 | 7.8 |
| 27 | 4 | 6 | 700 | 325 | 100 | 30 | 4.2 | 7.1 |
| 28 | 4 | 6 | 850 | 325 | 100 | 15 | 4.4 | 3.4 |
| 29 | 4 | 2 | 700 | 325 | 100 | 21 | 4.5 | 4.7 |
| 30 | 4 | 8 | 700 | 325 | 100 | 24 | 4.6 | 5.2 |
| 31 | 2 | 6 | 700 | 325 | 100 | 23 | 5.1 | 4.5 |
| 32 | 8 | 6 | 700 | 325 | 100 | 17 | 4.5 | 3.8 |
| 33 | 10 | 6 | 700 | 325 | 100 | 19 | 4.6 | 4.1 |
| 34 | 4 | 6 | 700 | 150 | 100 | 23 | 4.5 | 5.1 |
| 35 | 4 | 6 | 700 | 200 | 100 | 28 | 4.3 | 6.5 |
| 36 | 4 | 6 | 700 | 500 | 100 | 22 | 4.4 | 5.0 |
| 37 | 4 | 6 | 700 | 850 | 100 | 16 | 4.6 | 3.5 |
| 38 | 4 | 6 | 700 | 325 | 25 | 36 | 5.5 | 6.6 |
| 39 | 4 | 6 | 700 | 325 | 500 | 25 | 4.3 | 5.8 |
| 40 | 4 | 6 | 700 | 325 | 1000 | 16 | 4.3 | 3.7 |
| 41 | 4 | 6 | 550* | 325 | 100 | 39 | 11 | 3.5 |
| 42 | 4 | 6 | 900* | 325 | 100 | 10 | 5.0 | 2.0 |
| 43 | 4 | 1* | 700 | 325 | 100 | 17 | 8.1 | 2.1 |
| 44 | 4 | 10* | 700 | 325 | 100 | 12 | 5.1 | 2.4 |
| 45 | 1* | 6 | 700 | 325 | 100 | 16 | 7.3 | 2.2 |
| 46 | 12* | 6 | 700 | 325 | 100 | 20 | 8.1 | 2.5 |
| 47 | 4 | 6 | 700 | 325 | 10* | 53 | 14 | 3.8 |
| 48 | 4 | 6 | 700 | 325 | 1500* | 6 | 3.1 | 1.9 |

For each example, sixteen sensors were prepared. As for the previous examples, each sensor was heated to 325° C. by its heater and measurement of the electrical resistance of the sensor in clean air at 25° C. and the electrical resistance in an atmosphere containing 100 ppm $SiH_4$ gas at 25° C. was carried out 10 times. The results of measurements (average values for the 16 sensors of each example) are shown in Table 5. As before, $R_o$ is the initial resistance in air, $R_{g1}$ is the resistance upon the first exposure to $SiH_4$, and $R_{g10}$ is the resistance upon the 10th exposure.

As can be seen from the results of measurements on the comparative examples, if the molar ratio of Pt to Sn is below approximately 0.02 (Example 45) or above approximately 0.10 (Example 46), the value of $R_{g10}/R_{g1}$ is too large, indicating a large change in the sensitivity of the sensor over use.

If the molar ratio of Sb to Sn is less than approximately 0.02 (Example 43), the value of $R_{g10}/R_{g1}$ is too large, and if the molar ratio is greater than approximately 0.08 (Example 44), the value of $R_o/R_{g10}$ is too small.

If the calcining temperature in the oxidized antimony atmosphere is less than approximately 600° C. (Example 41), the value of $R_{g10}/R_{g1}$ is too large, and if the calcining temperature is greater than approximately 850° C. (Example 42), the value of $R_o/R_{g10}$ is too small.

If the $SiH_4$ gas atmosphere to which a sensor is exposed during preparation contains less than approximately 25 ppm of $SiH_4$ (Example 47), the value of $R_{g10}/R_{g1}$ is too large, and if the $SiH_4$ concentration is greater than approximately 1000 ppm (Example 48), the value of $R_o/R_{g1}$ is too small.

In contrast, all of examples 26-40 prepared according to the present invention had good initial sensitivity to $SiH_4$ ($R_o/R_{g1} \geq 10$), an acceptable change in sensitivity over use ($R_{g10}/R_{g1} \leq 5.5$), and a good sensitivity to $SiH_4$ after being used 10 times ($R_o/R_{g10} \geq 3$).

In order to measure the sensitivity of sensors according to the present invention to silane gases other than $SiH_4$, the resistance of sensors identical to Example 27 was measured in either $SiH_2Cl_2$ or $(CH_3)_3SiCl$. Sixteen sensors were prepared using the method of Example 27. The sensors were heated to 325° C. with their heaters, and the electrical resistance of each sensor in clean air at 25° C. ($R_0$) was measured. Eight of the sensors were then placed in an atmosphere containing 100 ppm $SiH_2Cl_2$ at 25° C. and the other eight sensors were placed in an atmosphere containing 100 ppm $(CH_3)_3SiCl$, and the resistance of each sensor ($R_g$) was measured. The results of measurements are shown in Table 6 and Table 7, Table 6 being for $SiH_2Cl_2$ and Table 7 being for $(CH_3)_3SiCl$.

TABLE 6

| Sensor No. | $R_o$ | $R_g$ | $R_o/R_g$ |
| --- | --- | --- | --- |
| 1 | 41.3 | 3.2 | 12.8 |
| 2 | 64.1 | 4.4 | 14.5 |
| 3 | 49.2 | 3.6 | 13.5 |
| 4 | 45.2 | 3.0 | 14.9 |
| 5 | 35.5 | 3.4 | 10.3 |
| 6 | 34.3 | 3.5 | 9.7 |
| 7 | 45.5 | 2.3 | 19.5 |
| 8 | 79.1 | 3.6 | 21.7 |
| Average | 49.3 | 3.4 | 14.6 |

TABLE 7

| Sensor No. | $R_o$ | $R_g$ | $R_o/R_g$ |
| --- | --- | --- | --- |
| 1 | 38.4 | 1.4 | 26.7 |
| 2 | 191.6 | 10.7 | 17.8 |
| 3 | 45.4 | 1.6 | 27.7 |
| 4 | 87.2 | 2.8 | 31.1 |
| 5 | 74.2 | 3.4 | 21.8 |
| 6 | 149.6 | 11.7 | 12.8 |
| 7 | 66.4 | 2.2 | 30.5 |
| 8 | 119.2 | 4.7 | 25.4 |
| Average | 96.5 | 4.8 | 24.2 |

EXAMPLES 49-60

To illustrate the effects of different concentrations of oxidized antimony in the oxidized antimony atmosphere used in calcining, Examples 49-60 of Tables 8 and 9 were prepared. Examples 49-54 were identical in composition and method of preparation to Example 25 of Table 5 except that the amount of SbOCl which was calcined to produce an oxidized antimony atmosphere was varied from 0.25 mg to 7.5 mg. (Example 52 exactly corresponds to Example 25). The effective volume in the quartz tube in which the SbOCl was calcined was 628 cm$^3$, so the concentrations of oxidized Sb in the quartz tube ranged from $2.3 \times 10^{-9}$ to $6.9 \times 10^{-8}$ moles/cm$^3$.

The examples of Table 9 were similar to those of Table 8 except that $Sb_2O_3$ was used in place of SbOCl. In this case the concentration of oxidized antimony ranged from $2.72 \times 10^{-9}$ to $8.2 \times 10^{-8}$ moles/cm$^3$.

TABLE 8

| Example No. | Amount of SbOCl | $R_o/R_g$ | Sb Concentration (moles/cm$^3$) |
| --- | --- | --- | --- |
| 49 | 0.25 mg | 14 | $2.3 \times 10^{-9}$ |
| 50 | 0.5 mg | 21 | $4.6 \times 10^{-9}$ |
| 51 | 1.0 mg | 26 | $9.2 \times 10^{-9}$ |
| 52 | 2.5 mg | 30 | $2.3 \times 10^{-8}$ |
| 53 | 5.0 mg | 18 | $4.6 \times 10^{-8}$ |
| 54 | 7.5 mg | 8 | $6.9 \times 10^{-8}$ |

TABLE 9

| Example No. | Amount of $Sb_2O_3$ | $R_o/R_g$ | Sb Concentration (moles/cm$^3$) |
| --- | --- | --- | --- |
| 55 | 0.25 mg | 12 | $2.7 \times 10^{-9}$ |
| 56 | 0.5 mg | 18 | $5.5 \times 10^{-9}$ |
| 57 | 1.0 mg | 23 | $1.1 \times 10^{-8}$ |
| 58 | 2.5 mg | 26 | $2.7 \times 10^{-8}$ |
| 59 | 5.0 mg | 17 | $5.5 \times 10^{-8}$ |
| 60 | 7.5 mg | 7.5 | $8.2 \times 10^{-8}$ |

For each example, 6 elements were prepared. Each of the elements was then heated to 325° C. by its heater and measurement of its electrical resistance in clean air at 25° C. ($R_o$) and its electrical resistance in an atmosphere containing 100 ppm $SiH_4$ at 25° C. ($R_g$) was performed.

As can be seen from both tables, if the concentration of oxidized antimony in the oxidized antimony atmosphere lies between approximately $1 \times 10^{-9}$ and $3 \times 10^{-8}$ moles/cm$^3$, the resulting element has good sensitivity to $SiH_4$ gas ($R_o/R_g \geq 10$). For this reason, the concentration of $SiH_4$ gas is defined as being approximately $2 \times 10^9$ to $6 \times 10^{-8}$ moles/cm$^3$, and preferably approximately $4 \times 10^{-9}$ to $4 \times 10^{-8}$ moles/cm$^3$.

In all of the preceding examples, when the sensors were exposed to a silane gas atmosphere subsequent to calcining, the silane gas atmosphere was at 25° C. and the sensors were heated by the electrical heaters installed therein. However, if during exposure the sensor is not heated but instead the silane gas atmosphere is heated to 150°-850° C., a sensor having the same characteristics as those described above can be obtained.

In the above-described examples, calcining either in air or in an oxidized antimony atmosphere was carried out for 30 minutes, and exposure to a silane gas atmosphere was carried out for 10 minutes. However, calcining may be performed for 5 to 50 minutes, and exposure to a silane gas atmosphere may be carried out for 2 to 60 minutes.

Whereas in the above examples the sensors were dried by natural drying after the application of a paste, drying may be performed in a constant temperature bath.

In the above examples, aging of the sensors was performed in unheated air and the sensors were heated by their heaters. Alternatively, a sensor may be aged in a constant temperature bath without use of the sensor heater.

As the solvent for preparing a paste, isopropyl alcohol was used in the above examples. However, other organic solvents may be used, such as an organic solvent comprising 25% by weight of beta-terpineol, 3% by weight of ethyl cellulose, and 72% by weight of butyl-carbitol acetate.

Whereas an alumina porcelain tube was used as a base for the above-mentioned paste in the above examples, an electrical insulator which can withstand calcining having a tubular, plate-like, or other shape can be used instead.

The heating means provided in the sensor may be a conventional electrical heater or may be an infrared lamp or the like.

In the above examples, the oxidized antimony atmosphere was prepared by calcining SbOCl or $Sb_2O_3$. Alternatively, the atmosphere may be prepared from solid or gaseous $SbCl_3$ or gaseous SbH or the like.

As the silane gas atmosphere to which sensors were exposed following calcining, $SiH_4$ in air was used in the above examples, However, $SiH_2Cl_2$, $(C_2H_5O)_4Si$, $SiCl_4$, $(CH_3)_2SiCl_2$, or other silane may be used instead of $SiH_4$.

What is claimed is:

1. A silane gas sensor comprising:
   a silane-sensitive element prepared by mixing $SnO_2$, SbOCl, and Pt such that the molar ratio of Sb to Sn is approximately 0.02-0.08 and the molar ratio of Pt to Sn is approximately 0.02-0.10, calcining the mixture at 600°-850° C., and exposing said element to a silane atmosphere wherein the concentration of silane gas is approximately 25-1000 ppm and wherein the temperature of the calcined mixture during the exposure step is about 150°-850° C. and means for heating said silane-sensitive element to about 200° to 400° C.

2. A process for making a silane gas sensor comprising the steps of:
   (a) adding an aqueous solution of $H_2PtCl_6$ to $SnO_2$ so that the molar ratio of Pt/Sn is approximately 0.02-0.10, thoroughly dispersing said $SnO_2$ in said $H_2PtCl_6$, followed by freezing and vacuum drying of the resulting dispersion;
   (b) mixing SbOCl with the product of Step (a) so that the molar ratio of Sb to Sn in the resulting mixture is approximately 0.02-0.08;
   (c) adding an organic solvent to the product of Step (b), forming the resulting mixture into a paste, coating the paste on an electrical insulator having electrodes, and drying said coated paste;
   (d) calcining said coated insulator product in Step (c) at approximately 600°-850° C. in air; and
   (e) exposing said calcined insulator of Step (d) to a silane atmosphere wherein the concentration of silane gas is approximately 25-100 ppm and wherein the temperature of the calcined insulator during the exposure step is about 150°-850° C.

3. A process for making a silane gas sensor comprising the steps of:
   (a) adding an aqueous solution of $H_2PtCl_6$ to $SnO_2$ so that the molar ratio of Pt/Sn is approximately 0.02-0.10, thoroughly dispersing said $SnO_2$ in said $H_2PtCl_6$, followed by freezing and vacuum drying of the resulting dispersion;
   (b) mixing SbOCl with the product of Step (a) so that the molar ratio of Sb to Sn in the resulting mixture is approximately 0.02-0.08;
   (c) adding an organic solvent to the product of Step (b), forming the resulting mixture into a paste, coating the paste on an electrical insulator having electrodes, and drying said coated paste;
   (d) calcining said coated insulator produced in Step (c) at approximately 600°-850° C. in an oxidized antimony atmosphere; and
   (e) exposing said calcined insulator of Step (d) to a silane atmosphere wherein the concentration of silane gas is about 25-1000 ppm and wherein the temperature of the calcined insulator during the exposure is about 150°-850° C.

4. A process as claimed in claim 3, wherein said oxidized antimony atmosphere is produced by calcining an antimony compound so that the concentration of oxidized antimony in said oxidized antimony atmosphere is approximately $2 \times 10^{-9}$ to $6 \times 10^{-8}$ moles/cm$^3$.

5. The process as claimed in claim 4 wherein the concentration of oxidized antimony in said oxidized antimony atmosphere is approximately $4 \times 10^{-9}$ to $4 \times 10^{-8}$ moles/cm$^3$.

* * * * *